United States Patent [19]

Itak et al.

[11] Patent Number: 5,411,869
[45] Date of Patent: May 2, 1995

[54] IMMUNOLOGICAL ANALOGS FOR CAPTAN

[75] Inventors: Jeanne A. Itak, Hamilton, N.J.; James R. Fleeker, Fargo, N. Dak.; David P. Herzog, Warrington, Pa.

[73] Assignee: Ohmicron Corporation, Newtown, Pa.

[21] Appl. No.: 22,283

[22] Filed: Feb. 25, 1993

Related U.S. Application Data

[62] Division of Ser. No. 830,594, Feb. 4, 1992, abandoned.

[51] Int. Cl.$^6$ ........................................... G01N 33/553
[52] U.S. Cl. .................................... 435/7.93; 435/967; 436/526; 436/815; 530/389.8; 530/391.3; 530/404; 530/405; 530/807
[58] Field of Search ................................ 436/526, 815; 530/391.3, 389.3, 807; 435/7.93, 967

[56] References Cited

U.S. PATENT DOCUMENTS 5,147,786  9/1992  Feng et al. ........................ 435/7.94

OTHER PUBLICATIONS

"Captan", publication of the Ohmicron Corp., Feb. 27, 1992.
J. Gosling, Clin. Chem., vol. 36, No. 8, 1408–1427 (1990) "A decade of development in Immunoassay Methodology".
N. Wolfe et al., J. Agric Food Chem., vol. 24, No. 5, 1041–1045 (1976), "Captan Hydrolysis".
W. Newsome et al., 203rd ACS Nat'l Meeting, San Francisco, Calif., Apr. 5–10, 1992, Abstr Pap Am Chem Soc 203 (1–3) 1992.

*Primary Examiner*—Mary E. Ceperley
*Attorney, Agent, or Firm*—Omri M. Behr; Matthew J. McDonald

[57] ABSTRACT

There is provided a standard for use in testing for captan in immunoassays. This standard has the structure THPD—$(CH_2)_x$—$(R^3)_y$—$R^1$ wherein THPD is cis-1,2,3,6-tetrahydrophthalimido, x is an integer from 1 to 10, $R^1$ selected from the group consisting of —COOH, —$NH_2$, —$NO_2$, —SH and —OH, $R^3$ is an aryl moiety and y is 0 or 1. Compounds of this general structure are known, they mimic the immunological reaction of captan and related compounds which are not stable in water and thus cannot be satisfactorily used as standards in testing for the presence and level of presence of captan and related compounds. There is also provided a method of carrying out such testing, utilizing such standards in which the standard (I) is coupled to a protein that is large enough to elicit an immune response in warm blooded animals, to yield compound (II). THPD—$(CH_2)_x$—$(R^3)_y$—$R^2$—[—$C^*$—]—[LP]   (II), wherein $C^{}$ is a coupling agent capable of coupling a member of the group $R^1$ to a protein, $R^2$ is the residue remaining when $R^1$ is coupled with coupling agent $C^{}$, $C^*$ is the residue remaining from coupling agent $C^{**}$ after coupling a member of the group $R^1$ to a protein and LP is a protein of sufficient size to generate an antibody response in a warm blooded animal.

8 Claims, No Drawings

IMMUNOLOGICAL ANALOGS FOR CAPTAN

This application is a division of application Ser. No. 07/830,594, filed Feb. 4, 1992, abandoned.

FIELD OF THE INVENTION

Hydrolytically stable immunological analogs for captan and captafol.

BACKGROUND OF THE INVENTION

Standard for use in testing for captan.

Environmental testing requirements call for the determination of low levels of the fungicide captan and the related captafol. These compounds are readily hydrolyzed and thus unstable in aqueous media. This instability makes it very difficult to devise standards for detecting small amounts of these materials by immunoassay. Captan has the structure THPD—S—CCl$_3$ and captafol has the structure THPD—S—CCl$_2$—CH.Cl$_2$, wherein THPD is the cis-1,2,3,6-tetrahydrophthalimido moiety. In order to carry out immunoassay tests for captan, which type of assay is most useful in detecting very small amounts of an unknown material, it would be necessary to provide a water stable analog of captan which is reactive with the antibody used in the method. It has been found by the work disclosed and claimed herein, that such a standard can be provided by a material having the structure THPD—(CH$_2$)$_x$—(R$^3$)$_y$—R$^1$   (I)

wherein THPD is cis-1,2,3,6-tetrahydrophthalimido, x is an integer from 1 to 10, R$^1$ selected from the group consisting of —COOH, —NH$_2$, —NO$_2$, —SH and —OH, R$^3$ is an aryl moiety and y is 0 or 1. Several compounds within this general structure wherein R$^1$ is carboxyl are reported in the literature, in particular those wherein x has the value 2, 1, 3, and 5. The method of synthesis involves the condensation of tetrahydrophthalic anhydride with an equimolar amount of the corresponding amino alkanoic acid. The literature however appears to be silent on any immunological relationship between compounds of formula (I) and captan or captafol.

SUMMARY OF THE INVENTION

There is provided a standard for use in testing for captan in immunoassays. This standard has the structure THPD—(CH$_2$)$_x$—(R$^3$)$_y$—R$^1$   (I)

wherein THPD is cis-1,2,3,6-tetrahydrophthalimido, x is an integer from 1 to 10, R$^1$ selected from the group consisting of —COOH, —NH$_2$, —NO$_2$, —SH and —OH, R$^3$ is an aryl moiety and y is 0 or 1. Compounds of this general structure are known, but heretofore it has not been known that in an immunoassay they mimic the immunological reaction of captans which are not stable in water and thus cannot be satisfactorily used as standards in testing for the presence and level of presence of captans.

There is also provided a method of carrying out such testing, utilizing such standards. In this methodology the standard (I) is coupled to a large protein, that is to say one large enough to elicit an immune response in warm blooded animals, using a coupling agent in techniques well known in the art, to yield compound (II).

THPD—(CH$_2$)$_x$—(R$^3$)$_y$—R$^1$+C**+[LP]→THPD—(CH$_2$)$_x$—(R$^3$)$_y$—R$^2$—[—C*—]—[LP]   (II)

wherein C is a coupling agent capable of coupling a member of the group R$^1$ to a protein, R$^2$ is the residue remaining when R$^1$ is coupled with coupling agent C, C* is the residue remaining from coupling agent C** after coupling a member of the group R$^1$ to a protein and LP is a protein of sufficient size to generate an antibody response in a warm blooded animal, such as a rabbit, suitably bovine serum albumin, keyhole limpet hemocyanin, ovalbumin, fibrinogen or thyroglobulin.

Anti-serum containing antibodies to compound (I) are obtained by administering an effective amount of compound (II) to a warm blooded test animal, permitting the immune system of said animal to generate antibodies thereto, bleeding said test animal to obtain its blood, and isolating the serum from said blood. It is not necessary to purify the serum, the antibodies in the serum are then coupled to separatable carrier particles, suitably paramagnetic particles are covalently coupled to the antibodies, for example glutaraldehyde coupling of antibodies to amine terminated particles may be employed.

The invention further discloses and requires a detection system (III), suitably an analogue of (II) wherein LP is an enzyme THPD—(CH$_2$)$_x$—(R$^3$)$_y$—R$^2$—[—C*—]—[EM]   (III)

wherein EM is an enzyme, suitably horseradish peroxidase.

Thus the invention discloses, in a process for calibrating a standard for the immunoassay of captan by incubation of a labeled captan standard, a captan standard and an antibody to captan, the improvement wherein the captan standard is THPD—(CH$_2$)$_x$—(R$^3$)$_y$—R$^1$ (I), the labeled captan standard is THPD—(CH$_2$)$_x$—(R$^3$)$_y$—R$^2$—[—C*—]—[EM] (III) and the antibody is obtained by administering an effective amount of compound (II) to a warm blooded test animal, permitting the immune system of said animal to generate antibodies thereto, bleeding said test animal to obtain its blood, and isolating the serum from said blood. The antibodies in the serum are then coupled to separatable carrier particles, suitably paramagnetic particles which are covalently coupled to the antibodies, for example glutaraldehyde coated particles may be used.

In the process for the immunoassay of an unknown sample of captan by incubation of said unknown captan sample or a captan standard, a labeled captan standard, and antibody to captan the improvement is also disclosed which comprises utilizing as the captan standard THPD—(CH$_2$)$_x$(R$^3$)$_y$—R$^1$ (I), as the labeled captan standard THPD—(CH$_2$)$_x$(R$^3$)$_y$—R$^2$—[—C*—]—[EM] (III) and the aforementioned separatable, suitably paramagnetic, particles covalently coupled to the antibodies of the anti-serum. The process comprises the steps of incubating a plurality of captan standard samples, each containing a fixed concentration of antibody, a fixed concentration of labeled captan standard and a different known concentration of captan standard, preparing a standard curve from said standard samples, incubating a sample containing an unknown concentration of captan, a fixed concentration of antibody and a fixed concentration of labeled captan standard and determining the amount of captan in said sample from said standard curve.

DESCRIPTION OF THE PREFERRED EMBODIMENTS

The standard which is used for use in testing for captan immunoassays has the structure

$$THPD-(CH_2)_x-(R^3)_y-R^1 \qquad (I)$$

wherein THPD is phthalimido, x is cis-1,2,3,6-tetrahydro an integer from 1 to 10, suitably 1 to 5. Thus $(CH_2)_x$ is methyl, ethyl, propyl, isopropyl, butyl, isobutyl, terbutyl, or pentyl. $R^1$ is a group such as $-COOH$, $-NO_2$, $NH_2$, $-SH$ or $-OH$. $R^3$ is aryl, suitably mono or bicyclo aryl such as substituted or unsubstituted phenyl or naphthyl. It is clear from the foregoing formula that the $R^3$ group may be present or absent. When present, it will be substituted by $R^1$ but may also be substituted by other substituents which are not sensitive to the coupling agent $C^{}$. Among these substituents of which there may be one or more, may be included alkyl, suitably lower alkyl of 1–5 carbon atoms, chloro, fluoro, bromo, and trifluoromethyl. As coupling agents $C^{}$, there may be employed coupling agents which couple to the LP protein and either remain in situ as a link or disappear. Coupling agents, depending on the active groups on the protein (enzyme) and the ligand, include sodium meta-periodate (Schiff's base formation), carbodiimides: 1-ethyl-3-(3-dimethylaminopropyl)carbodiimide, N,N'-dicyclohexylcarbodiimide, 1-cyclohexyl-3-(2-morpholinylethyl)carbodiimide), N-hydroxysuccinimide by formation of an N-hydroxysuccinimide ester using a carbodiimide, m-maleimidobenzoyl-N-hydroxysuccinimide ester, succinimidyl 4-(N-maleimidomethyl)cyclohexane-1-carboxylate, N-succinimidyl 3-(2-pyridyldithio)propionate and formation of diazonium salts by slow addition of nitrous acid. The most suitable coupling agents are dicyclohexylcarbodiimide and 1-ethyl-3-(3-dimethylaminopropyl)carbodiimide.

Thus, the standard is coupled to LP, a protein of sufficient size to generate an antibody response in a warm blooded animal, such as a rabbit, suitably bovine serum albumin, keyhole limpet hemocyanin, ovalbumin, fibrinogen or thyroglobulin, by methods known to those skilled in the art for the appropriate coupling agents.

In another embodiment of the invention, LP may be an enzyme EM. Most suitable as enzyme may be horseradish peroxidase, however, the invention is not limited thereto. There may also be employed beta-galactosidase, alkaline phosphatase, urease, glucose oxidase.

In the preferred procedure tetrahydrophthalic anhydride is condensed with a bifunctional moiety of formula $(CH_2)_x-(R^3)_y-R^1$. It will be understood by those skilled in the art that such a procedure may be employed where $R^1$ is COOH, $NO_2$, and SH. In this general process the tetrahydrophthalic anhydride and the reactant $NH_2-(CH_2)_x-(R^3)_y-R^1$ are taken up in a suitable, polar anhydrous medium preferably an alkanoic acid, for example glacial acetic acid, warmed on a steam bath and the solvent substantially removed. The residue is taken up in a low boiling reaction inert organic solvent such as, methylene chloride, washed with water, dried, solvent removed and the residue taken up in an azeotropic solvent such as, toluene. An acid catalyst, suitably paratoluene sulfonic acid is added and the reaction completed by reflux with a Dean-Stark water trap. The resultant solution is cooled, concentrated, diluted with a low boiling alkane solvent suitably, hexane to produce an oil which then crystallizes and is re-crystallized.

Where the $R^1$ group is hydroxy the starting material is not the tetrahydrophthalic anhydride but rather the corresponding tetrahydrophthalimide itself. This is dissolved in an alkanoic solution of an alkali metal alkoxide suitably, sodium methoxide in methanol. The solvent is removed by evaporation and the corresponding haloalkanol suitably, the bromoalkanol is added to the solid directly. After completion of the initial reaction the total reactants are taken up in a suitable, reaction inert organic solvent for example, dimethylformamide and the reaction completed by heating under reflux for several hours suitably, from 4 to 10 hours. The reaction mixture is then quenched in water, extracted with a suitable water immiscible reaction inert organic solvent such as methylene chloride, dried, concentrated, and the resultant hydroxy derivative crystallized from the extract, suitably by partial precipitation of the addition of an alkane solvent such as hexane.

Where $R^1$ is amino there are two possible synthetic routes. In the first, the corresponding compound wherein $R^1$ is COOH is converted into the corresponding acid chloride suitably by reaction with oxalyl chloride or the like, which is then taken up in a reaction inert organic solvent, suitably relatively high boiling solvent, such as toluene and again evaporated to remove any residual oxalyl chloride. The acid chloride is then taken up in a dry reaction inert organic solvent, suitably a hydrocarbon solvent such as benzene and heated, under reflux, with an alkaline metal azide, suitably sodium azide. The precipitated sodium chloride is removed by filtration, the solvent evaporated, the residue stirred in dilute aqueous mineral acid to convert the isocyanate to the corresponding amine, filtered, made alkaline and immediately extracted with a water immiscible reaction inert organic solvent such as methylene chloride. The solvent extract is dried and the thus produced amine is precipitated as the hydrochloride salt by passage of dry hydrogen chloride gas into the solution.

In an alternate procedure where the combination $(R^3)_y-R^1$ is an aryl as opposed to an alkyl amino group the corresponding compound wherein $R^1$ is nitro is produced in accordance with the initial procedure. The aryl nitro group is then reduced to the corresponding amino group by procedures which will not affect the carboxy groups or the degree of unsaturation on the phthalimido moiety. A suitable agent for this purpose is aqueous acidic ferrous sulfate. The reaction is quenched with aqueous ammonium hydroxide and the product isolated by pouring the entire mixture onto an excess of cracked ice.

The immunogen is prepared by coupling a compound of general Formula I with a protein of sufficient size to generate an antibody response in a warm blooded animal such as a rabbit. Any of the aforementioned coupling agents may be employed by methods well known to those skilled in the art, especially suitably dicyclohexyl- and ethyldimethylaminopropyl carbodiimides. In the standard procedure the captan standard is taken up in dry dioxane, cooled, isobutylchloroformate and the tributylamine added and the solution added slowly to an aqueous buffered solution of the protein. Purification is by dialysis followed by freeze drying.

The enzyme conjugate may be prepared by similar methods. For enzymes however, it is preferable to utilize N-hydroxysuccinimide and dicyclohexylcarbodiimide in dimethylformamide, together with the captan standard (I). The precipitated dicyclohexylurea is removed and the DMF solution of the conjugate ester is stored at reduced temperatures, suitably between about −10° to about −30° C. The reaction is completed by adding the enzyme, such as horseradish peroxidase, in alkaline sodium carbonate for example, to the solution. The reaction takes place at room temperature in about 4 to about 12, suitably in about 8 hours and the enzyme conjugate (III) is separated from the uncoupled standard (I) by elution from a Sephadex column with phosphate buffered saline.

The anti-serum is produced by taking up the captan immunogen in a suitable injectable carrier, for example sterile saline, preferably in the presence of adjuvant such as Freud's complete adjuvant and injected into the warm-blooded antibody generating animal, such as a rabbit. Booster injections are made at around day 20 and day 45 after the initial injection. Bleeding for serum production is carried out between 7-10 days after the final immunization. After collection, the blood is permitted to clot, the clots separated from the collection vessel, stored overnight at about 4° C., and the serum removed therefrom by conventional methods such as centrifugation. The thus produced serum is anti-serum containing antibodies against the captan standard.

This anti-serum is coupled directly to BioMag amine terminated particles. The captan standard assay applies the principals of enzyme linked immunoabsorbent assay (ELISA). The determination of captan by the methodology is set forth hereinbelow.

EXPERIMENTAL

Example 1—Preparation of Captan Standard Compound (I)

6-(cis-1,2,3,6-tetrahydrophthalimido)hexanoic acid (1a)

31 g (0.2 mole) of cis-1,2,3,6-tetrahydrophthalic anhydride and 26.2 g (0.2 mole) of 6-aminohexanoic acid are dissolved in 400 ml. of acetic acid and warmed 3 hours on a steam bath. The cooled solution is concentrated to remove most of the acetic acid and the residue taken up in 200 ml. of methylene chloride. The solution is washed twice with water and dried over sodium sulfate. The solvent is removed and the residue taken up in 500 ml toluene. Para-toluenesulfonic acid (1 g) is added to the solution, followed by reflux for 10 hrs. with a Dean-Stark water trap. The solution is cooled and concentrated to about 50 ml and diluted with 50 ml of hexane. The mixture is shaken for a few minutes until the oil crystallizes then cooled at 4° C. for several hours, filtered and dried at 50° C. The light yellow crystals (32 g) are taken up in chloroform and filtered to remove any precipitate. The solution is diluted with hexane near the cloud point, cooled until a crystalline mass accumulates, filtered and dried to yield white crystals, m.p. 85°–87° C.

$^1$H NMR (CDCl$_3$) 1.3(m, 2H, CH$_2$); 2.3(m, 4H, 2CH$_2$); 2.65((m, 2H, CH$_2$); 3.1(t, 2H, 2CH); 3.5(t, 2H, CH$_2$CO$_2$); 5.9(m, 2H, CH=CH); 11.0(s, 1H, COOH). $^{13}$C NMR(CDCl$_3$) 180.1, 179.8, 127.9, 39.1, 38.9, 34.8, 28.2, 26.0, 24.2, 23.6.

3-(cis-1,2,3,6-tetrahydrophthalimido)-1-propanol (1b)

15.1 g. of cis-1,2,3,6-tetrahydrophthalimide are dissolved in 15 ml of methanol in which has previously been dissolved, 2.3 g of sodium metal. The mixture is evaporated to dryness under reduced pressure. 14 g. of 3-bromo-1-propanol are added to the solid, warming occurs. When the heating subsides, 40 ml of dimethylformamide are added with heating under reflux for 6 hours. After cooling, 200 ml of water and 100 ml of methylene chloride are added. The mixture is shaken and the aqueous phase discarded. The organic extract is washed with water (2×50 ml) and the methylene chloride solution is dried over anhydrous sodium sulfate. The solution is concentrated to about 50 ml and hexane added near the cloud point. Cooling to 0° C. precipitates 3-(cis-1,2,3,6-tetrahydrophthalimido)-1-propanol (1b).

5-(cis-1,2,3,6-tetrahydrophthalimido)-1-pentylamine, hydrochloride salt (1c)

13.25 g of 6-(cis-1,2,3,6-tetrahydrophthalimido)hexanoic acid (1a) is warmed under reflux for 3 hours with 50 ml of oxalyl chloride. The excess oxalyl chloride is removed by warming under reduced pressure. The resulting acid chloride residue is taken up in 20 ml toluene and the solution take to dryness again. The acid chloride is refluxed overnight with stirring, in 200 ml dry benzene and 3.8 g sodium azide. After cooling, the precipitated sodium chloride is removed by filtration and the filtrate taken to dryness by warming under reduced pressure. The residue is suspended in 100 ml of 2M HCl with stirring. The mixture is stirred 5 hours at room temperature. The pH is adjusted to distinctly alkaline with 3M NaOH, then immediately extracted with methylene chloride (3×50 ml). The combined extracts are dried over anhydrous sodium sulfate. The salt filtered off and dry HCl gas passed into the solution. After precipitation is complete, the hydrochloride salt of 5-(cis-1,2,3,6-tetrahydrophthalimido)-1-pentylamine (1d) is filtered off, washed with methylene chloride and stored in the dark and protected from moisture.

3-(cis-1,2,3,6-tetrahydrophthalimido)-1-propylmercaptan (1d)

15.1 g of cis-1,2,3,6-tetrahydrophthalic anhydride are added to 500 ml of toluene followed by 9.1 g of 3-mercapto-1-propylamino. Heating with stirring under reflux continues for 16 hours, using a water trap. The yield is improved if the reaction is carried out under nitrogen. The mixture is cooled. Most of the solvent is removed by warming under reduced pressure. 3-(cis-1,2,3,6-tetrahydrophthalimido)-1-propylmercaptan (1e) is precipitated by addition of hexane followed by filtration by suction and drying under reduced pressure.

6-cis-1,2,3,6-tetrahydrophthalimido)-1-(4-nitrophenyl)ethane (1e)

16.6 g of p-nitrophenethylamine and 15.1 g. of cis-1,2,3,6-tetrahydrophthalic anhydride are heated under reflux in 500 ml of toluene, with stirring and a water trap, for 16 hours. The reaction is cooled and take to dryness by warming under reduced pressure. Recrystallization from ethanol-water yields 1-(cis-1,2,3,6-tetrahydrophthalimido)-1-(4-nitrophenyl) ethane (1e).

4-(cis-1,2,3,6-tetrahydrophthalimidoethyl)aniline (1f)

16.6 g of p-nitrophenethylamine and 15.1 g of cis-1,2,3,6-tetrahydrophthalic anhydride are heated under reflux in 300 ml of toluene, with stirring and a water trap, for 16 hours. This mixture is cooled and take to dryness by warming under reduced pressure. The residue is transferred to a flask containing 500 ml of water, 270 g ferrous sulfate heptahydrate and 1.3 ml concentrated hydrochloric acid. Steam is delivered to the mixture. When the temperature reaches 90° C., 75 ml of concentrated ammonium hydroxide is added in one portion, and at two-minute intervals three 25 ml portions of ammonium hydroxide are added. Continue stirring and heating during the additions. The total reaction time is 8–10 minutes. Immediately pour the mixture onto 1 kg of cracked ice. The solid is collected by filtration and washed with water. Recrystallize from water ethanol to obtain -4-(cis-1,2,3,6-tetrahydrophthalimidoethyl) aniline (1f).

Example 2: Preparation of Immunogen (II)

37 mg (0.14 mmole)of a captan standard compound (I), 6-(cis-1,2,3,6-tetrahydrophthalimido)hexanoic acid (1a), are dissolved in 9 ml of dry diozane. After cooling the solution, 0.47 ml of 0.3M tributylamine in dioxane is added with stirring, followed by 0.47 ml of 0.3M isobutylchlorformate in dixano. Cool another 5 minutes, then stir without cooling 35 minutes. The dioxane solution is added dropwise over a 25–30 minute period to a stirred solution of 95 mg of thyroglobulin in 10 ml of 0.2M sodium borate, pH 8.7 at 0° C. After the addition is complete, stir another 30 minutes with cooling then remove the ice-bath and stir an additional 4 hours. Dialyze against 0.3M sodium chloride and 0.1M sodium phosphate, pH 7.4 overnight at 25° C., then dialyze against distilled water for 8 hours. Freeze dry.

Estimation of the degree of substitution is with 2,4,6-trinitrobenzene sulfonic acid which detects amino groups. The difference in response between the conjugate and unconjugated thyroglobulin represents the proportion of amino groups which are conjugated. (Hazra, et al., (1984) *Anal. Biochem.* 137:437–443). The resulting compound was estimated to contain approximately 65 captan standard molecules/molecule of immunogen.

Example 3: Preparation of Enzyme Conjugate (III)

Dicyclohexylcarbodiimide (42 mg, 0.2 mmole) is dissolved in 0.5 ml. DMF. Add this solution dropwise to a stirred solution of captan ligand (I) (53 mg, 0.2 mmole) and N-hydroxysuccinimide (23 mg., 0.2 mmole) in 4 ml of DMF at 4° C. The reaction mixture is allowed to warm to room temperature and stirred overnight. The reaction mixture is centrifuged to remove the precipitated dicyclohexylurea. The active ester may be stored at −20° C. in a container sealed from moisture.

20 μl of the active ester (25 mg, $6.6 \times 10^{-7}$ mole)in DMF are placed into a 12×75 mm test tube. 0.5 ml. Horseradish Peroxidase (3 mg, $6.6 \times 10^{-8}$ mole) in 0.5M sodium carbonate, pH 9.5 are added to the solution. Additional DMF may be necessary to clarify the reaction mixture. The mixture is allowed to stand for 8 hours at room temperature. Finally, using a Sephadex G-25 column (1×20 cm) the enzyme conjugate (III) is separated from uncoupled ligand (I) by elution with 0.1M phosphate buffer saline.

Example 4: Immunization Protocol—Captan Standard Antiserum

The captan immunogen produced in Example 2 is dissolved or suspended in sterile saline to a concentration of 4 mg/ml. and mixed with an equal amount of Freund's complete adjuvant and emulsified in the usual fashion.

| | |
|---|---|
| Day 1 | A total of 0.5 ml. of the emulsion is injected into hip muscle of rabbit. Also a control bleeding is carried out. |
| Day 20 | Back of animal is shaved and in 6–8 sites a total of 0.5 ml. of the emulsion is injected. |
| Day 30 | Test bleed. |
| Day 45 | Immunization repeated as done on Day 20. |
| Day 55 | Test bleed. |

Immunization described on Day 20 is repeated at 30 day intervals using Freund's incomplete adjuvant. This interval may be lengthened if antibody production is adequate or animal is distressed.

Bleeding is carried out 7–10 days after the final immunization (30–50 ml).

Example 5: Antiserum Production

After collection, blood should be allowed to clot for 30–60 minutes at 37° C. The clot should then be separated from the sides of the collection vessel using a Pasteur pipette or some similar instrument. Place the clot at 4° C. overnight to allow it to contract. The serum should then be removed from the clot and any remaining insoluble material removed by centrifugation at 10,000×g for 10 minutes at 4° C. After preparation, the antiserum can be stored for many years at −20° C. or colder.

Example 6: Procedure for Coupling Captan Antiserum to Magnetic Particles

BioMag 4100 amine terminated particles (Advanced Magnetics, 1 ml of approximately 50 mg/ml) are activated with 5% (v/v) glutaraldehyde in 0.01M MES buffer, pH 6 (2 ml). Unreacted glutaraldehyde is removed by washing with 0.01M MES buffer. The rabbit anti-captan serum (IV) is diluted to approximately 5 mg Ab/ml and is reacted with the activated magnetic particles. 1M glycine solution is then used to quench any unreacted sites and the particles are diluted and stored in 25 mM Tris/150 mM NaCl/0.1% BSA/15 ppm active Kathon/1 mM EDTA (V).

Example 7: Test Methodology for Detection of Captan and Captofol

Principle

The Captan Standard Assay applies the principles of enzyme linked immunosorbent assay (ELISA) to the determination of captan. The sample to be tested is added, along with an enzyme conjugate (III), to a disposable test tube followed by magnetic particles with antibodies specific to captan attached (V). Both the captan (which may be in the sample) and the enzyme labeled captan standard (III) (in the enzyme conjugate) compete for antibody sites on the magnetic particles (V). At the end of the incubation period, a magnetic field is applied to hold the magnetic particles (with captan and labeled captan standard bound to the antibodies on the particles, in proportion to their original concentration)in the tube and allow the unbound reagents to be decanted. After decanting, the particles are washed with washing solution.

The presence of captan to bound enzyme labeled captan standard (III) is detected by adding a mixture of the enzyme substrate (hydrogen peroxide) and the chromogen (3,3′,5,5′-tetramethylbenzidine). The enzyme labeled captan standard attached to the captan antibody catalyzes the conversion of the substrate/chromogen mixture to a colored product. After an incubation period, the reaction is stopped and stabilized by the addition of acid. Since the labeled captan standard was in competition with the unlabeled (sample) captan for the antibody sites, the color developed is inversely proportional to the concentration of captan in the sample.

The test system utilizes the following components:

Reagents

1. Captan Antibody Coupled Magnetic Particles (V).
2. Captan Enzyme Conjugate

The horseradish peroxidase (HRP)labeled captan standard (III) is supplied in 25 mM Tris, 150 mM NaCl, pH 7.4 containing 0.1% (w/v) bovine serum albumin. The concentration of conjugate (III) is determined empirically based on performance in the assay.

3. Captan Standards

Three levels of calibrators (I) equivalent to 0.08, 0.35 and 1.30 ppm of captan in 25 mM Tris, 150 mM NaCl, 0.1% (w/v) bovine serum albumin, 1ram EDTA and 15 ppm Kathon at pH 6.0.

4. Control

A level approximately equivalent to 0.16 ppm of captan in 25 mM Tris, 150 mM NaCl, 0.1% (w/v) bovine serum albumin, and 1 mM ethylenediaminetetraacetic acid at pH 6.0.

5. Diluent/Zero Standard 25 mM Tris, 150 mM NaCl, 0.1% (w/v) bovine serum albumin, and 1 mM ethylenediaminetetraacetic acid at pH 6.0.

6. Peroxide Solution

Hydrogen peroxide (0.02%) in a citric acid buffer at pH 4.5.

7. Chromogen (TMB) Solution 3,3',5,5'-tetramethylbenzidine (0.4 g/l) in 26% dimethylformamide.

8. Stopping Solution

A solution of sulfuric acid (2M).

9. Washing Solution

Preserved deionized water.

10. Test Tubes

Polystyrene tubes.

In addition to the reagents, the following items are essential for the performance of the test:

| | |
|---|---|
| Pipets* | Precision pipets capable of delivering 100, 250 and 500 µl and a 1.0 ml repeating pipet. |
| Vortex Mixer* | Thermolyne Maxi Mix, Scientific Industries Vortex Genie, or equivalent. |
| Magnetic Separation Unit* | |
| Photometer* | RPA-I TM RaPID ® Photometric Analyzer or equivalent photometer capable of readings at 450 nm. |

*These items are available from Ohmicron.

To reduce the rate of captan hydrolysis, it is recommended that once samples are prepared in diluent, they be kept on ice and assayed as soon as possible. All other reagents, including the standards and control, must be at room temperature prior to use.

Proper dilution of samples and/or other modifications to the samples may be required. Dilution of samples should be made using an appropriate amount of Diluent/Zero Standard and mixed thoroughly before assaying. All methods should be validated.

Reagent Preparation

The Color Reagent is prepared just prior to use by combining the Chromogen and Peroxide Solutions. To calculate the total amount (ml) of Color Reagent required, the number of tubes which will be used is multiplied by 0.66. Then equal volumes (half the amount needed, i.e., number of tubes×0.33 ml) are mixed in a clean glass tube. The Color Reagent should remain clear.

All reagents must be allowed to come to room temperature and the Antibody Coupled Magnetic Particles mixed thoroughly before use. The antibody should not be transferred to glass containers.

Procedural Notes and Procedures

The reagents are added directly to the bottom of the tubes while avoiding contact between the reagents and the pipet tip. This will help assure consistent quantities of reagent in the test mixture. Cross-contamination and carryover of reagents is avoided by using clean pipets for each sample addition and by a voiding contact between reagent droplets on the tubes and pipet tips. Foam formation during vortexing is also undesirable.

The RaPID ® Magnetic Separator consists two parts: an upper rack which will securely hold the test tubes and a lower separator which contains the magnets used to attract the antibody coupled magnetic particles. During incubations the upper rack is removed from the lower separator so that the magnetic particles remain suspended during the incubation. For separation steps, the rack and the separator are combined to pull the magnetic particles to the sides of the tubes. To obtain optimum assay precision. It is important to perform the separation steps carefully and consistently. The rack is decanted by inverting away from the operator using a smooth turning action so the liquid flows consistently along only one side of the test tube. While still inverted, the rack is placed on an absorbent pad and allowed to drain. Lifting the rack and replacing gently into the pad several times will ensure complete removal of the liquid from the rim of the tube. The Antibody Coupled Magnetic Particles (V) should be is just prior to pipeting.

| Assay Procedures | |
|---|---|
| 1. Label test tubes for standards, control and samples. | |
| Tube Number | Contents of Tube |
| 1,2 | Diluent/Zero Standard, 0 ppm |
| 3,4 | Standard 1, 0.08 ppm |
| 5,6 | Standard 2, 0.35 ppm |
| 7,8 | Standard 3, 1.30 ppm |
| 9 | Control |
| 10 | Sample 1 |
| 11 | Sample 2 |
| 12 | Sample 3 |

2. Add 200 µl of the appropriate standard (I), control, or sample.

3. Add 250 µl of Captan Enzyme Conjugate (III) to each tube.

4. Mix the Captan Antibody Coupled Magnetic Particles thoroughly and add 500 µl to each tube.

5. Vortex for 1 to 2 seconds minimizing foaming.

6. Incubate for 30 minutes at room temperature.

7. Separate in the RaPID ® Magnetic Separator for two (2) minutes.

8. Decant and gently blot al tubes briefly in a consistent manner.

9. Add 1 ml. of Washing Solution to each tube and allow them to remain in the magnetic separation unit for two (2) minutes.

10. Decant and gently blot all tubes briefly in a consistent manner.
11. Repeat Steps 9 and 10 an additional time.
12. Remove the rack from the separator and add 500 μl of freshly prepared Color Reagent to each tube.
13. Vortex for 1 to 2 seconds minimizing foaming.
14. Incubate for 20 minutes at room temperature.
15. Add 500 μl of Stopping Solution to each tube.
16. Read results at 450 nm within 15 minutes after adding the Stopping Solution.

Results

Manual Calculations

1. Calculate the mean absorbance value for each of the standards.
2. Calculate the % B/Bo for each standard by dividing the mean absorbance value for the standard by the mean absorbance value for the Diluent/Zero Standard.
3. Construct a standard curve by plotting the % B/Bo for each standard on vertical logit (Y) axis versus the corresponding captan concentration on horizontal logarithmic (X) axis on the log-logit paper provided.
4. % B/Bo for controls and samples will then yield the standard curve.

RPA-I ™ RaPID ® Photometric Analyzer

By using the RPA-I ™ RaPID ® Photometric Analyzer, calibration curves can be automatically calculated and stored. To obtain results from this Assay on the RPA-I ™ the following parameter settings are recommended:
Data Reduct: Lin. Regression
Xformation: Ln/LgtB
Read Mode: Absorbance
Wavelength: 450 nm
Units: PPM
Rgt Blk: 0
Concentrations:
1:0.00 PPM #2:0.08 PPM #3:0.35 PPM #4:1.30 PPM
Range: 0.02–1.50
Correlation: 0.990
Rep. % CV: 10%

Performance Data Specificity

The cross-reactivity of the Captan RaPID ® Assay for various phthalamide fungicides and metabolites can be expressed as least detectable dose (LDD) which is estimated at 90% B/Bo.

| Compound | LDD (ppm) |
| --- | --- |
| Captan | 0.01 |
| Captafol | 1.00 |
| Folpet | 8.60 |
| Tetrahydrophthalimide | 10.00 |
| Phthalimide | >10.00 |
| Metolachlor | 2.00 |
| Propachlor | 5.00 |
| Carbaryl | 5.00 |
| Alachlor | 10.00 |

In addition, the following compounds demonstrated no reactivity in the Assay at concentrations up to 10 ppm; aldicarb, aldicarb sulfoxide, aldicarb sulfone, ametryn, atrazine, benomyl, burylate, carbofuran, cyanazine, 2,4-D, desethylatrazine, 1,3-dichloropropane, dinoseb, MCPA methomyl, metribuzin, pentachlorophenol, phosphamidon, picloram, procymidone, prometron, prometryn, propazine, terbufos, terbutryn, terbutylazine, thiabendazole, and thiophanate-methyl.

Sensitivity

The Captan RaPID ® Assay has an estimated minimum detectable concentration, based on a 90% B/Bo, of 0.1 ppm.

Recovery

Water samples were spiked with various levels of captan, frozen, and assayed using the Captan RaPID ® Assay. The following results were obtained:

| Amount of Captan Added (ppm) | Mean (ppm) | S.D. (ppm) | % |
| --- | --- | --- | --- |
| 0.10 | 0.11 | 0.02 | 110 |
| 0.25 | 0.28 | 0.01 | 112 |
| 0.50 | 0.55 | 0.06 | 110 |
| 1.00 | 1.10 | 0.18 | 110 |
| Average | | | 111 |

Precision

The following results were obtained:

| Control | 1 | 2 | 3 |
| --- | --- | --- | --- |
| Replicates | 10 | 10 | 10 |
| Days | 5 | 5 | 5 |
| N | 50 | 50 | 50 |
| Mean | 0.08 | 0.32 | 0.83 |
| % CV (within assay) | 17.7 | 8.4 | 9.2 |
| % CV (between assay) | | 13.1 | 4.45.5 |

We claim:

1. In a process for calibrating a standard for the immunoassay of captan by incubation of a labeled captan standard, a captan standard and an antibody to captan, including the steps of forming an antigen-antibody complex, detecting this complex, and correlating the amount of complex formed with the concentration of the standard, the improvement wherein the captan standard is THPD—(CH$_2$)$_x$—R$^1$ 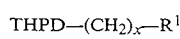

wherein THPD is cis-1,2,3,6-tetrahydrophthalimido, x is an integer from 1 to 10, and R$^1$ is selected from the group consisting of —COOH, —NH$_2$, —NO$_2$, —SH and —OH.

2. In a process for calibrating a standard for the immunoassay of captan by incubation of a labeled captan standard, a captan standard and an antibody to captan, including the steps of forming an antigen-antibody complex, detecting this complex, and correlating the amount of complex formed with the concentration of The standard, the improvement wherein the captan standard is THPD—(CH$_2$)$_x$—R$_1$ 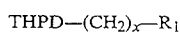

wherein THPD is cis-1,2,3,6-tetrahydrophthalimido, x is an integer from 1 to 10, and R$^1$ is selected from the group consisting of —COOH, —NH$_2$, —NO$_2$, —SH and —OH, wherein the labeled captan standard is the product of the reaction THPD—(CH$_2$)$_x$—R$^1$ + C** + EM → THPD—(CH$_2$)$_x$—R$^2$—[—C*—]—[EM]

wherein
EM is an enzyme,
C* is the residue remaining from a coupling agent C**, which is capable of coupling a member of the group R$^1$ of THPD—(CH$_2$)$_x$—R$^1$ to enzyme EM, and
R$^2$ is the residue remaining when R$^1$ is coupled to EM with coupling agent C**.

3. In a process for calibrating a standard for the immunoassay of captan by incubation of a labeled captan standard, a captan standard and an antibody to captan, including the steps of forming an antigen-antibody complex, detecting this complex, and correlating the amount of complex formed with the concentration of the standard, the improvement wherein the captan standard is THPD—(CH$_2$)$_x$—R$^1$ wherein the labeled captan standard is THPD—(CH$_2$)$_x$—R$^2$—[—C*—]—[EM]

wherein
EM is horseradish peroxidase and,
C*, THPD, x, R$^1$, and R$^2$ are as defined in claim 2.

4. In a process for calibrating a standard for the immunoassay of captan by incubation of a labeled captan standard, a captan standard and an antibody to captan, including the steps of forming an antigen-antibody complex, detecting this complex, and correlating the amount of complex formed with the concentration of the standard the improvement wherein the captan standard is THPD—(CH$_2$)$_x$—R$^1$ wherein the labeled captan standard is THPD—(CH$_2$)$_x$—R$^2$[—C*—]—[EM]

wherein
C*, THPD, EM, R$^1$, R$^2$, and x are as defined in claim 2, wherein the antibodies are the antibodies to captan covalently coupled to paramagnetic particles.

5. A process for the immunoassay of an unknown sample of captan by incubation of said unknown captan sample, a labeled captan standard, a captan standard and an antibody to captan, wherein the captan standard is THPD—(CH$_2$)$_x$—R$^1$ wherein the labeled captan standard is THPD—(CH$_2$)$_x$—R$^2$—[—C*—]—[EM]

wherein
C*, THPD, EM, R$^1$, R$^2$ and x are as defined in claim 4, wherein the antibodies are the antibodies coupled to paramagnetic particles as defined in claim 4, comprising the steps of incubating a plurality of captan standard samples, each containing a fixed concentration of antibody, a fixed concentration of said labeled captan standard and a different known concentration of said captan standard, preparing a standard curve from said standard samples, incubating a sample containing an unknown concentration of captan, a fixed concentration of antibody, a fixed concentration of said labeled captan standard, and determining the amount of captan in said sample from said standard curve.

6. The process of claim 5 wherein R$^1$ is —COOH.
7. The process of claim 6 wherein x is 5.
8. The process of claim 7 wherein EM is horseradish peroxidase.

* * * * *